(12) United States Patent
Verhoeven

(10) Patent No.: US 6,658,664 B1
(45) Date of Patent: Dec. 9, 2003

(54) VISOR CAP WITH SELECTIVELY REVEALABLE CONCEALED ADJUSTMENT BAND

(76) Inventor: Jason Verhoeven, 5880 W. 8th St., #1, Los Angeles, CA (US) 90036

(*) Notice: Subject to any disclaimer, the term of this patent is extended or adjusted under 35 U.S.C. 154(b) by 18 days.

(21) Appl. No.: 10/159,034

(22) Filed: Jun. 1, 2002

(51) Int. Cl.7 .................................................. A61F 9/00
(52) U.S. Cl. .................................. 2/12; 2/181; 2/195.1
(58) Field of Search ........................... 2/12, 171, 175.1, 2/181, 195.1, 195.2, 195.3, 195.4, 195.5, 183, 181.4, 209.13, 417, 418, 420; D2/865, 872, 873, 893, 894; 24/442, 445

(56) References Cited

U.S. PATENT DOCUMENTS

| | | | | |
|---|---|---|---|---|
| 4,918,758 A | * | 4/1990 | Rendina | 2/171 |
| 5,519,892 A | | 5/1996 | Pizzacar | 2/195.2 |
| 5,548,845 A | | 8/1996 | Gallup | 2/195.2 |
| 5,584,076 A | | 12/1996 | Armstrong | 2/195.2 |
| 5,600,855 A | | 2/1997 | Ramirez | 2/209.13 |
| 5,996,116 A | | 12/1999 | Tate | 2/12 |
| 6,006,362 A | | 12/1999 | Walsh | 2/209.13 |
| 6,016,572 A | * | 1/2000 | Park | 2/195.2 |
| 6,049,911 A | | 4/2000 | Bromberg | 2/195.3 |
| 6,119,273 A | | 9/2000 | Cho | 2/195.3 |
| 6,446,266 B1 | * | 9/2002 | Park | 2/195.1 |

* cited by examiner

Primary Examiner—Gary L. Welch
(74) Attorney, Agent, or Firm—Goldstein & Lavas, P.C.

(57) ABSTRACT

A visor cap, having a bill, a forehead shield having sides, an adjustable strap attached to and extending between the forehead shield sides, and a non-elastic sleeve. The adjustable strap extends through the non-elastic sleeve and has a relaxed position having a relaxed position length such that when in the relaxed position the non-elastic sleeve abuts the forehead shield sides. The adjustable strap has a pair of display panels adjacent to the forehead shield sides, and an elastic strap extending between the display panels. When the cap is donned by a wearer, the adjustable sleeve stretches to accommodate the head of the wearer, creating temple openings between the non-elastic sleeve and the forehead shield sides, revealing the display panels. When the cap is removed by the wearer, the elastic band returns to the relaxed position and the non-elastic sleeve once again abuts the forehead shield sides—substantially concealing the display panels.

8 Claims, 4 Drawing Sheets

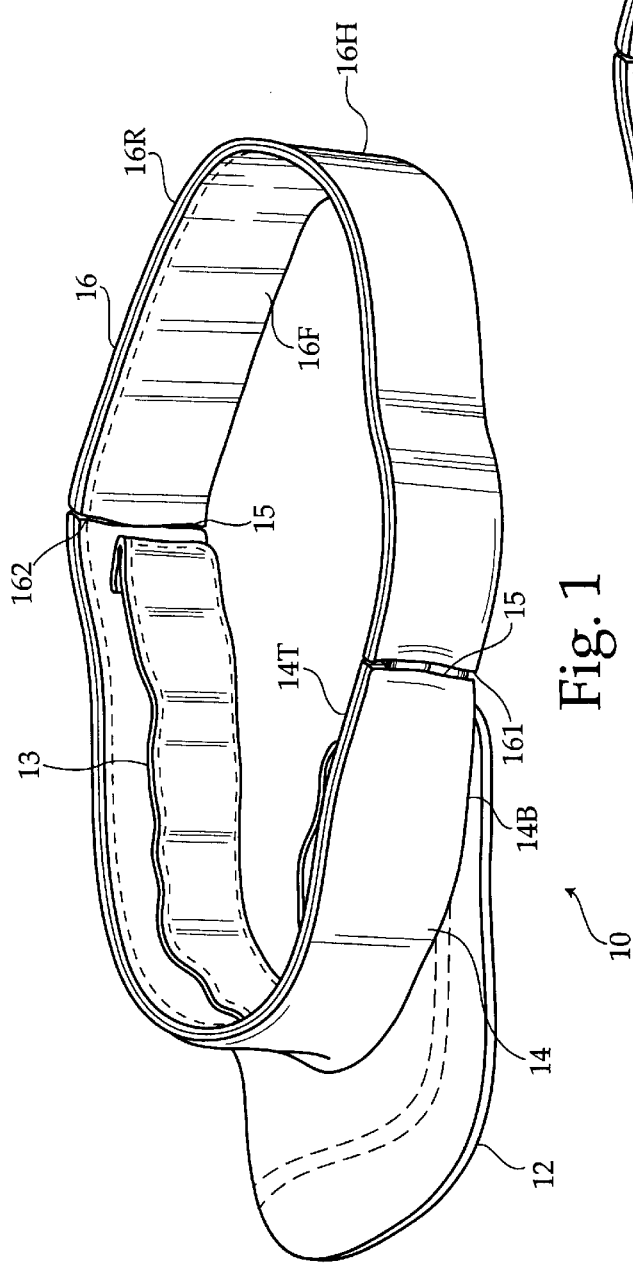
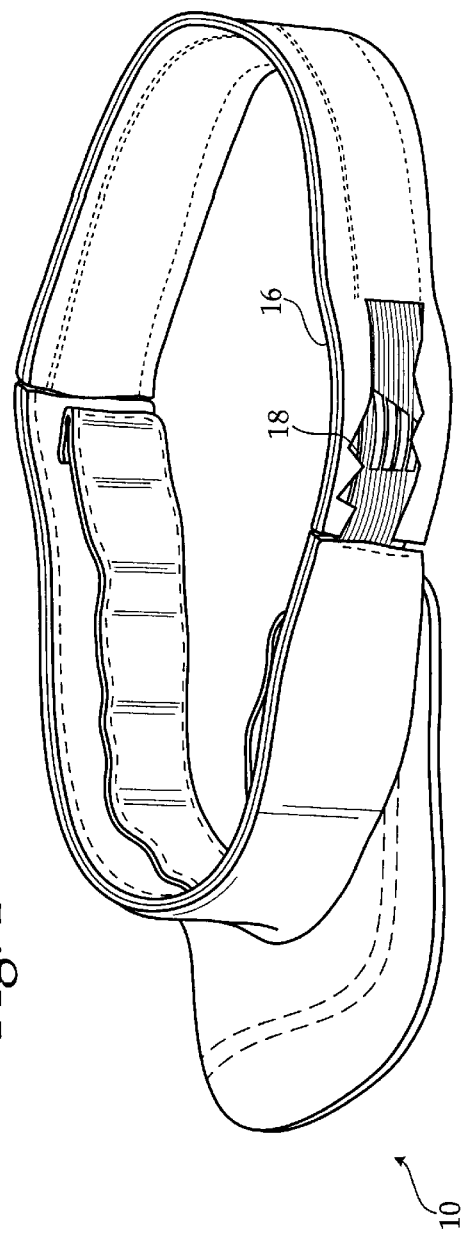

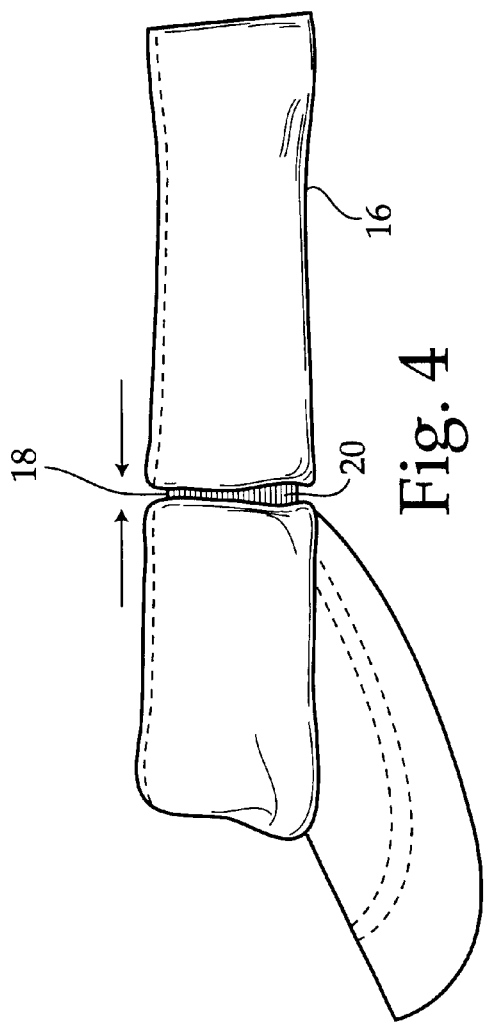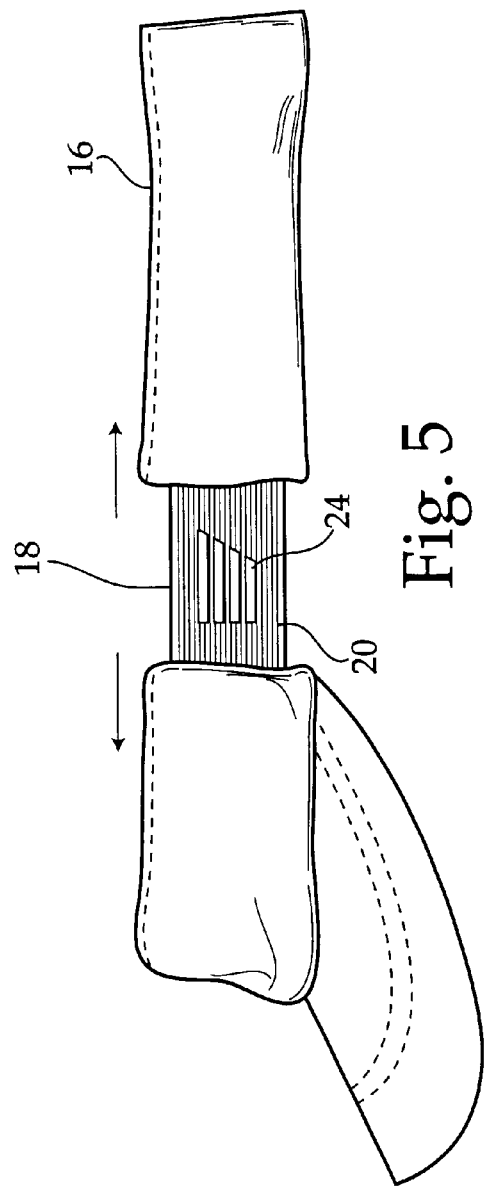

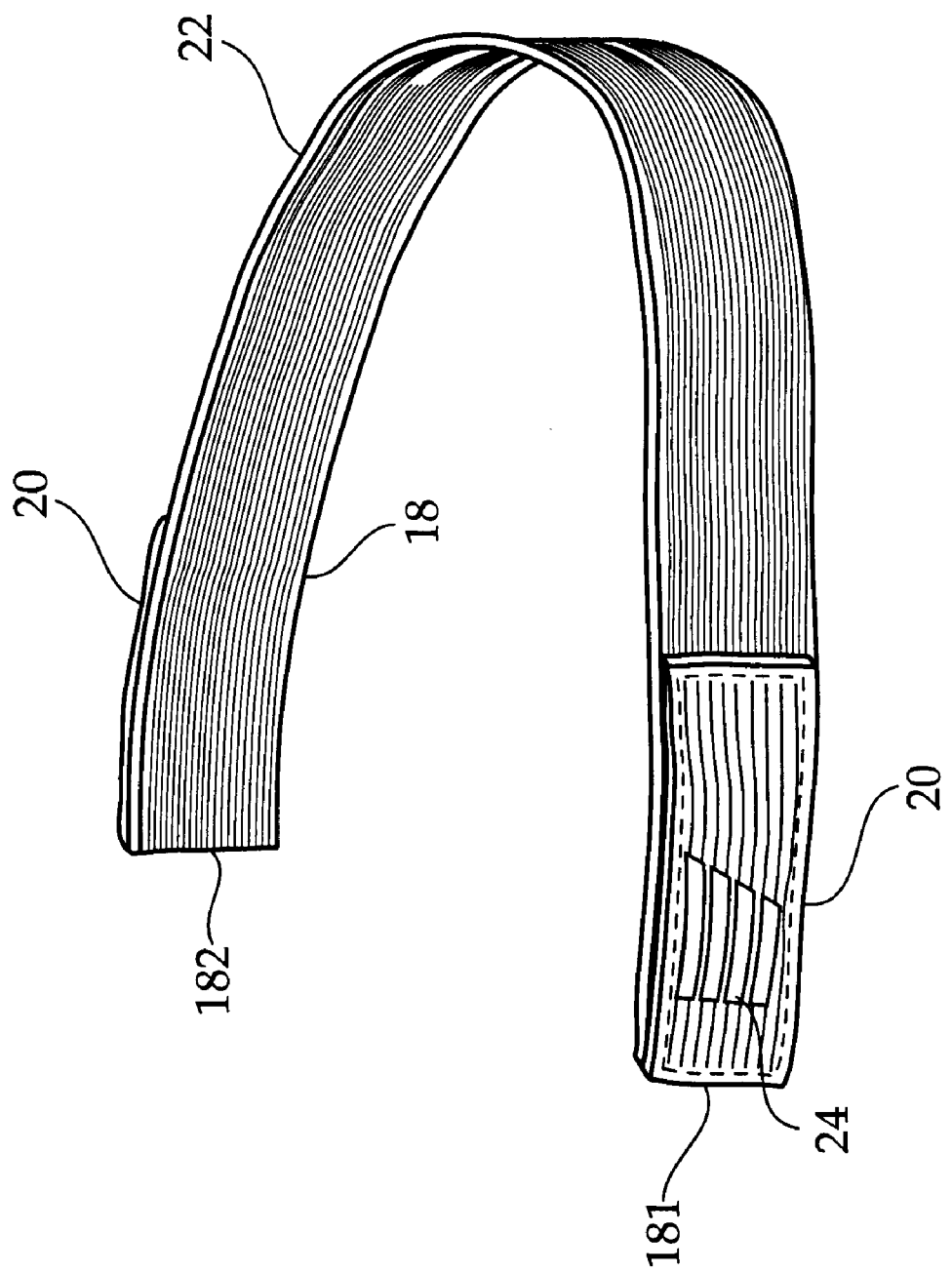

VISOR CAP WITH SELECTIVELY REVEALABLE CONCEALED ADJUSTMENT BAND

BACKGROUND OF THE INVENTION

The invention relates to a visor cap with a selectively revealable concealed adjustment band. More particularly the invention relates to a visor cap having an adjustment band which is normally concealed within a non-elastic rearwardly extending sleeve, such that when the cap is expanded in diameter as it is donned by a wearer, the adjustment band is selectively revealed at two side openings.

Although hats are worn for a variety of purposes, in the context of many sports, hats are worn primarily to keep the sun out of the athlete's eyes and to prevent sweat from the head from reaching the eyes and face of the athlete. In this regard, the common baseball hat has been available and in use for countless years.

In recent years, the "visor cap" has come into favor, and has replaced the baseball cap in certain circles. The visor cap encircles the head like a baseball cap, and shades the eyes from the sun with a bill like a baseball cap, but is open on top to both allow the head to dissipate heat and to avoid disheveling the hair of the wearer as severely as a baseball cap would.

When it comes to visors, or hats in general, the phrase "one size fits all" clearly does not apply. Accordingly, nearly all sport hats have some type of adjustment mechanism. The ubiquitous baseball hat provides a plastic snap tab assembly with an open back having plastic tabs attached to the ends of the rim adjacent to the open back. Size adjustment is accomplished by overlapping the plastic tabs, which snap together with different discrete degrees of overlap. However, not only is the snap assembly unsightly and cheap looking, but it does not always provide a comfortable fit since the most comfortable position for certain wearers might exist between available overlap positions. In addition, in the case of the visor cap, such an adjustment mechanism ruins the otherwise seamless appearance of the rear band extending around the back of the head.

Others have attempted to provide solutions with regard to providing adjustability for a baseball cap. For example, U.S. Pat. No. 5,584,076 to Armstrong discloses an adjustable cap having a fully removable adjustment strap. Armstrong employs a strap which may be inserted the brim of the hat through an upper opening of the brim on the inside of the hat after it has been extending around the back of the wearer's head, and then is held in place by hook and loop fasteners (VELCRO).

U.S. Pat. No. 5,548,845 to Gallup discloses an adjustable closed-back cap. Gallup has a short sleeve at the rear of the cap which allows a strap to extend through the sleeve to make a desired adjustment, wherein the strap is attached to the rim exterior at an opposite side of the sleeve using hook and loop fasteners (VELCRO).

U.S. Pat. No. 6,119,273 to Cho discloses a free-size cap with a size adjusting band. In particular, Cho is an open back baseball cap wherein the strap may be fastened at any position by using a buckle.

While these units may be suitable for the particular purpose employed, or for general use, they would not be as suitable for the purposes of the present invention as disclosed hereafter.

In addition, since baseball caps and visors are often highly visible, worn not only by sports figures on the sports field or the golf course during televised events, but are worn by numerous other people on the street in their day-to-day activities. Accordingly, advertising on baseball caps and visors by presenting logos of various types is considered to be an important undertaking. In many cases providing effective advertising through the cap can by itself justify the manufacturing cost of the cap.

Accordingly, many have sought ways in which to use the cap to provide advertising. The most common way is to provide advertising indicia on the forehead shield of the cap. However, other attempts have been made, including U.S. Pat. No. 5,519,892 to Pizzacar; U.S. Pat. No. 5,600,855 to Ramirez; and U.S. Pat. No. 6,006,362 to Walsh—all of which seek to attach onto the overlapping plastic adjustment tabs at the rear of the ubiquitous baseball cap, to use the same as advertising space. Such units may also be suitable for the particular purpose for which they are employed, or for general use, but would not be as suitable for the purposes of the present invention as disclosed hereafter.

Accordingly, what is desired is to provide a cap which is adjustable in a convenient, comfortable, and visibly appealing manner, while providing the ability to advertise or otherwise display a logo or indicia in a clever manner such that it is visible yet unobtrusive.

SUMMARY OF THE INVENTION

It is an object of the invention to produce a visor cap which is adjustable to fit heads of varying sizes in an inconspicuous and unobtrusive manner. Accordingly, the visor cap has a rearwardly extending adjustable band which is attached and extends between both sides of the forehead shield. When in a relaxed, non-stretched position, the adjustable band is concealed within a closed, rearwardly extending non-elastic sleeve which is not attached to the forehead shield.

It is a further object of the invention to provide a visor cap which allows a logo or other indicia to be selectively displayed. Accordingly, the adjustable band has a pair of display panels nearest to the forehead shield, such that as the adjustable band is expanded when the hat is donned by the user, the display panels and any logo or indicia thereon are partially or fully revealed as the adjustable band expands onto the head of the user and the non-elastic sleeve is urged rearward.

The invention is a visor cap, having a bill, a forehead shield having sides, an adjustable strap attached to and extending between the forehead shield sides, and a non-elastic sleeve. The adjustable strap extends through the non-elastic sleeve and has a relaxed position having a relaxed position length such that when in the relaxed position the non-elastic sleeve abuts the forehead shield sides. The adjustable strap has a pair of display panels adjacent to the forehead shield sides, and an elastic strap extending between the display panels. When the cap is donned by a wearer, the adjustable sleeve stretches to accommodate the head of the wearer, creating temple openings between the non-elastic sleeve and the forehead shield sides, revealing the display panels. When the cap is removed by the wearer, the elastic band returns to the relaxed position and the non-elastic sleeve once again abuts the forehead shield sides—substantially concealing the display panels.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

FIG. 1 is a diagrammatic perspective view of the visor cap of the present invention, wherein the cap and adjustable band are at rest, and the adjustable band is not stretched such that temple openings, between the non-elastic band and the sides of the forehead shield, are substantially closed.

FIG. 2 is a diagrammatic perspective view, similar to FIG. 1, wherein the cap is at rest, except wherein a portion of the non-elastic sleeve has been broken away to reveal the display panel of the adjustable band and indicia printed thereon.

FIG. 4 and FIG. 5 both illustrate how the relative movement of the non-elastic sleeve toward and away from the forehead shield sides acts to both reduce and expand the temple openings and conceal and reveal the display panel and the indicia or logo printed thereon.

FIG. 6 is a diagrammatic perspective view, illustrating just the adjustable band which extends fully between the forehead visor, showing how the adjustable band can be made having an elastic band extending between the display panels, with the display panels laminated, layered, or otherwise attached thereon.

DETAILED DESCRIPTION OF THE PREFERRED EMBODIMENTS

Figure 3:
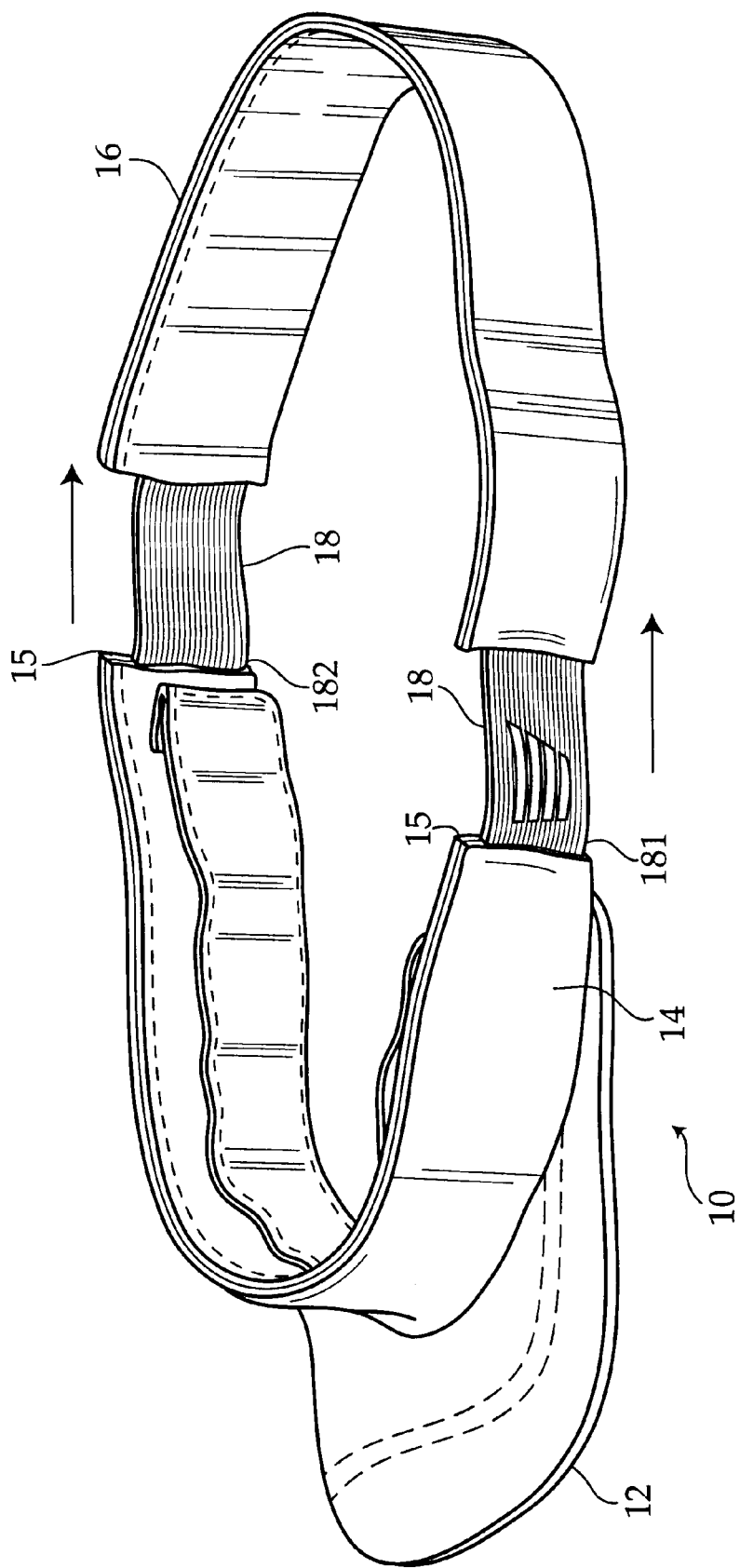
FIG. 3 is a diagrammatic perspective view, illustrating how when the non-elastic sleeve is urged rearward, the temple openings are expanded as the adjustable band stretches to reveal the display panels adjacent to the temple openings.

FIG. 1 illustrates a visor cap 10, for use by a wearer having a head having a head front and head rear. The visor cap 10 conventionally has a forwardly extending bill 12 and a forehead shield 14 having a shield top 14T and a shield bottom 14B, wherein the bill 12 extends forwardly from the shield bottom 14B. The forehead shield 14 has a pair of vertical forehead shield sides 15 having a forehead shield side height defined as the vertical distance between the shield top 14T and shield bottom 14B at the forehead shield sides 15. A sweat band 13 is attached immediately behind the forehead shield 14, extending horizontally substantially between the shield sides 15 and substantially parallel to the shield 14, such that the sweat band 13 seeks to catch and absorb sweat traveling down the forehead. In addition, a non-elastic sleeve 16 extends rearwardly from each of the shield sides 15 to as to fully encircle the head of the wearer. The non-elastic sleeve 16 has a sleeve height 16H which is substantially the same as the forehead shield side height so as to provide a substantially uniform and continuous appearance fully around the cap. In addition, the sleeve 16 made of a sleeve front panel 16F and a sleeve rear panel 16R which are stitched together to create a tunnel therebetween. The elongated sleeve 16 is substantially closed between the sleeve first end 161 and sleeve second end 162, the adjustable band 18 except at the sleeve first end 161 and sleeve second end 162. Additionally, the sleeve 16 is substantially flat and broad as seen in FIG. 1.

Unexpectedly however, the non-elastic sleeve 16 is not physically attached to the shield sides 15. In particular, the non-elastic sleeve 16 has a sleeve first end 161 and a sleeve second end 162 which typically abut yet are not attached to the shield sides 15. Accordingly, as seen in FIG. 2, an adjustable strap 18 extends through the non-elastic sleeve 16, and is freely longitudinally movable therein. Referring to FIG. 3, the adjustable strap 18 extends between and is fixedly attached to the shield sides 15. In particular, the adjustable strap 18 has a strap first end 181 and a strap second end 182, each of which are attached to one of the shield sides. Referring again to FIG. 1 and FIG. 2, the adjustable strap 18 has a relaxed position, when minimal or no longitudinal forces are being exerted on it, at which point it has a relaxed length. The non-elastic sleeve 16 is substantially the same in length as the relaxed length of the adjustable strap 18. Accordingly, the non-elastic sleeve 16 "floats" on the adjustable strap 18, yet when the adjustable strap is relaxed, the non-elastic sleeve first end 161 and second end 162 nearly or substantially abut the shield sides. An opening created between the non-elastic sleeve at either the first end 161 or second end 162 and its adjacent shield side may be termed a "temple opening", as the temple opening would roughly correspond with the temples of the wearer when donned. In the manner previously described then, when the adjustable strap 18 is relaxed, the temple openings are minimal.

However, referring to FIG. 3, when the non-elastic sleeve 16 is urged rearward, the adjustable strap 18 elongates, while the non-elastic sleeve does not. Accordingly, the first end 161 and second end 162 of the non-elastic sleeve move rearwardly and away from the shield sides 15, enlarging the temple openings and revealing the adjustable strap 18. In this regard, when donned by a wearer, typically, the non-elastic sleeve would be placed against the back of the wearer's head, while the cap 10 is pulled forward by the bill 12 or forehead shield 14, thus stretching the adjustable strap 18 until an overall diameter created by the forehead shield, non-elastic sleeve 16 and adjustable strap 18 that is long enough to permit the forehead shield 14 to be extended over the front of the wearer's head, and then rest comfortably theragainst. It is of course the stretching of the adjustable strap 18 which allows the cap 10 to fit snugly on wearer's having various head sizes.

Referring now to FIG. 6, the adjustable strap 18 may be constructed to take advantage of the fact that it is selectively revealed at the temple openings as it is elongated to fit the head of the wearer. Accordingly, a pair of display panels 20 are located at each of the strap first end 181 and strap second end 182. An elastic band 22 extends between the display panels and is then stitched, laminated, or otherwise attached to the display panels 20. Accordingly, the display panels 20 may themselves be non-elastic, while the elastic band 22 provides the stretchability of the adjustable strap 18. What is important, is that the adjustable strap 18 is capable of elongating between the strap first end 181 and strap second end 182 to increase its length by virtue of a longitudinal force exerted thereon to provide the adjustability of the cap. Further in accordance with maintaining the substantially broad and flat appearance of the non-elastic sleeve, since the adjustable strap 18 extends through the tunnel thereof, the adjustable strap 18 is itself substantially broad and flat.

Also illustrated on FIG. 6, the display panels may be decorated in a way that it contrasting with the elastic band 22, in color, design, or texture. Preferably though, it is desirable to place indicia 24 on the display panels, which may be a logo depicting a commercial or non-commercial entity, slogan, design, trademark of the like. However, as seen in FIG. 4 and FIG. 5, as the adjustable band 18 elongates and the non-elastic sleeve 16 moves rearward, the display panel 20 and the indicia 24 printed thereon is selectively revealed and concealed as the temple opening is enlarged or reduced.

In conclusion, herein is presented a visor cap which is adjustable to fit wearers having various size heads, and which allows the selective display of a logo or other indicia as the cap expands to fit onto the head. The invention is illustrated by example in the drawing figures and in the foregoing description. However, numerous variations are possible while adhering to the inventive concept. Such variations are contemplated as being a part of the present invention.

What is claimed is:

1. A visor cap, for being worn by a user, having a head, comprising:

a forehead shield having a pair of sides;

an adjustable strap having a first end and a second end, the first end attached to one of the sides of the forehead shield, the second end attached to the other of the sides of the forehead shield, the adjustable strap having a relaxed position having a relaxed length and capable of stretching into an extended position wherein it has an extended length;

a non-elastic sleeve having a sleeve first end and a sleeve second end, the non-elastic sleeve substantially the same in length as the relaxed length of the adjustable strap, the adjustable strap extending through the non-elastic sleeve fully between the sleeve first end and sleeve second end such that when the adjustable strap is in a relaxed state the non-elastic sleeve first end and second end substantially abut the sides of the forehead shield but are not attached thereto and the adjustable strap is concealed within the non-elastic sleeve, when the adjustable strap is in the extended position, temple openings are created between of the sides of the forehead shield and the non-elastic shield which reveal a portion of the adjustable strap.

2. The visor cap as recited in claim 1, wherein the adjustable strap has a pair of display panels and an elastic strap extending between the display panels, each display panel located at one of the adjustable strap first end and second end, each of the display panels bearing indicia which is thereby selectively visible as the temple openings are expanded as the adjustable strap is extended as the non-elastic sleeve first end and second end move away from the forehead shield sides.

3. The visor cap as recited in claim 2, wherein the cap has a bill extending forward from the forehead shield and a sweat band extending behind and substantially parallel to the forehead shield extending substantially between the forehead shield sides.

4. The visor cap as recited in claim 3, wherein the forehead shield has a shield side height at the sides of the shield, and wherein the non-elastic sleeve has a sleeve height which is substantially the same as the shield side height to provide a substantially continuous appearance when the adjustable strap is relaxed.

5. The visor cap as recited in claim 4, wherein the adjustable strap is substantially broad and flat, and wherein the non-elastic sleeve is substantially broad and flat.

6. A visor cap method, for use by a wearer, having a head having a head front and a head rear, using a cap having a forehead shield having a pair of sides, an adjustable strap attached to and extending between the pair of sides having a relaxed position having an relaxed position length and an extended position, and a non-elastic sleeve which extends between and abuts the sides of the forehead shield when the adjustable strap is in the relaxed position, comprising the steps of:

placing the non-elastic sleeve against the head rear;

stretching the adjustable strap by pulling the forehead shield forward until the forehead shield can be pulled downward over the forehead front wherein the step of stretching the adjustable strap further comprises revealing the adjustable strap by creating temple openings between the non-elastic sleeve and the forehead shield sides.

7. The visor cap method as recited in claim 6, wherein the adjustable strap has a pair of display panels and an elastic strap extending between the display panels, the display panels having indicia thereon, wherein the step of creating temple openings further comprises revealing the indicia on the display panels between the non-elastic sleeve and the forehead shield sides.

8. The visor cap method as recited in claim 7, wherein the visor has a bill extending forwardly from the forehead shield, and further comprising the step of concealing the display panels by closing the temple openings by removing the cap from the head of the wearer and allowing the adjustable band to return to the relaxed state and urging the non-elastic band to extend fully between and abut the sides of the forehead shield.

* * * * *